(12) United States Patent
Brehm

(10) Patent No.: US 8,257,294 B2
(45) Date of Patent: Sep. 4, 2012

(54) BLOOD TREATMENT DEVICE COMPRISING ROD-SHAPED MEANS FOR HOLDING ARTICLES

(75) Inventor: Winfried Brehm, Hofheim (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 389 days.

(21) Appl. No.: 11/664,790

(22) PCT Filed: Sep. 10, 2005

(86) PCT No.: PCT/EP2005/009766
§ 371 (c)(1),
(2), (4) Date: Dec. 27, 2010

(87) PCT Pub. No.: WO2006/037429
PCT Pub. Date: Apr. 13, 2006

(65) Prior Publication Data
US 2009/0005719 A1  Jan. 1, 2009

(30) Foreign Application Priority Data
Oct. 6, 2004  (DE) .................. 10 2004 048 911

(51) Int. Cl.
| A61M 37/00 | (2006.01) |
| B01D 29/00 | (2006.01) |
| F16M 13/00 | (2006.01) |
| F16M 11/00 | (2006.01) |
| A47F 5/00 | (2006.01) |
| A47F 7/00 | (2006.01) |

(52) U.S. Cl. .................. 604/5.01; 210/241; 248/125.7; 248/425

(58) Field of Classification Search ................. 604/5.01; 210/241, 249
See application file for complete search history.

(56) References Cited

U.S. PATENT DOCUMENTS

| 2,682,932 | A | * | 7/1954 | Howard ............................ 188/5 |
| 2,696,963 | A | * | 12/1954 | Shepherd ................. 248/229.15 |
| 2,969,150 | A | * | 1/1961 | Broman .................. 210/321.74 |
| 3,077,613 | A | * | 2/1963 | Mayer ............................ 482/139 |
| 4,585,436 | A | | 4/1986 | Davis et al. |

(Continued)

FOREIGN PATENT DOCUMENTS

CN  2538347  3/2003

(Continued)

OTHER PUBLICATIONS

Ronco, C., et al., "Critical Care Nephrology," Critical Care Nephrology, pp. 1269-1308, 1998.

*Primary Examiner* — Tatyana Zalukaeva
*Assistant Examiner* — Susan Su
(74) *Attorney, Agent, or Firm* — Jacobson Holman PLLC

(57) ABSTRACT

A blood treatment machine has a housing and a blood treatment module to hold components of an extracorporeal blood circulation. The machine simplifies access to a securing means for securing objects, in particular containers such as bags containing medicinal fluids, that is attached to a rod-shaped means attached to the blood treatment machine. Vertical and horizontal directions are defined by the orientation of the housing during the use of the blood treatment machine. The rod-shaped means has at least one first section and a second section, whereby the axial extent in the second section runs in a different direction than in the first section. In another embodiment, the rod-shaped means has a cropped course.

20 Claims, 1 Drawing Sheet

U.S. PATENT DOCUMENTS

| | | | |
|---|---|---|---|
| D339,195 S * | 9/1993 | Nash et al. | D24/128 |
| 5,375,276 A * | 12/1994 | Nelson et al. | 5/620 |
| 5,556,065 A * | 9/1996 | Wadley | 248/129 |
| 5,641,144 A * | 6/1997 | Hendrickson et al. | 248/292.13 |
| D381,745 S * | 7/1997 | Owens | D24/128 |
| 5,653,681 A | 8/1997 | Ellingboe | |
| 5,895,571 A | 4/1999 | Utterberg | |
| 6,056,249 A * | 5/2000 | Fillon, Jr. | 248/125.7 |
| 6,071,258 A * | 6/2000 | Dalke et al. | 604/5.01 |
| D437,640 S * | 2/2001 | Breda et al. | D24/128 |
| 6,315,751 B1 * | 11/2001 | Cosgrove et al. | 604/5.01 |
| 6,689,053 B1 * | 2/2004 | Shaw et al. | 600/227 |
| 6,730,220 B2 * | 5/2004 | McCartney | 210/241 |
| 6,796,955 B2 * | 9/2004 | O'Mahony et al. | 604/6.11 |
| 6,852,280 B2 * | 2/2005 | Vijay et al. | 422/45 |
| 7,022,099 B2 * | 4/2006 | Litzie et al. | 604/6.09 |
| 7,189,352 B2 * | 3/2007 | Carpenter et al. | 422/45 |
| 7,198,751 B2 * | 4/2007 | Carpenter et al. | 422/45 |
| 7,201,870 B2 * | 4/2007 | Olsen et al. | 422/44 |
| 7,204,958 B2 * | 4/2007 | Olsen et al. | 422/44 |
| 7,219,021 B2 * | 5/2007 | Liu et al. | 702/50 |
| 7,335,334 B2 * | 2/2008 | Olsen et al. | 422/45 |
| 2004/0154966 A1 | 8/2004 | Meziere et al. | |
| 2009/0284108 A1 * | 11/2009 | Castellano et al. | 312/209 |

FOREIGN PATENT DOCUMENTS

| | | | |
|---|---|---|---|
| JP | 56171054 U * | 5/1980 | |
| JP | 56-171054 | 12/1981 | |
| JP | 63-018143 | 1/1988 | |
| JP | 63018143 U * | 2/1988 | |

* cited by examiner

BLOOD TREATMENT DEVICE COMPRISING ROD-SHAPED MEANS FOR HOLDING ARTICLES

CROSS-REFERENCE TO RELATED APPLICATION

This is a national stage of PCT/EP05/009766 filed Sep. 10, 2005 and published in German.

BACKGROUND OF THE INVENTION

1. Field of Invention

The invention relates to the field of blood treatment machines having a housing and a blood treatment module.

2. Description of the Prior Art

The invention relates to the field of blood treatment machines according to the preamble of claim 1.

A wide variety of devices are used for extracorporeal blood treatment. Such a blood treatment device has a blood treatment module and in many cases also has other modules. The blood treatment module is suitable for holding the components of an extracorporeal blood circulation. With the help of such an extracorporeal blood circulation, usually in the form of disposable items intended for a single use, blood is taken from a patient and circulated via a blood supply line to a blood treatment element returned from there back to the patient via a blood return line. For example, the blood treatment element may be a hemofilter or hemodialyzer for renal replacement therapy, divided by a semipermeable membrane into two chambers, one chamber having the extracorporeal blood flow through it. In this case the other chamber is used to remove substances that are to be removed and/or liquid and in the case of hemodialysis a cleaning fluid may flow through it.

However, other blood treatment elements are also conceivable, such an oxygenator for artificial respiration or a blood absorption element for removal of certain substances from the extracorporeal blood by adsorption on suitably prepared surface elements.

For this purpose, the blood treatment module has sensors and/or actuators such as pumps and/or valves to detect components of the extracorporeal blood circulation, to control the blood treatment accordingly and monitor it.

With such blood treatments it may be necessary to keep the solutions that are in containers, in particular in bags, ready for use during the blood treatment. Such solutions may be solutions that are needed directly for the blood treatment itself, such as dialysis solution in the case of hemodialysis treatment or substituate solution in the case of hemofiltration treatment. However, the containers and/or solutions may also be those needed only in certain situations, e.g., when complications occur. For example, there may be a sudden drop in blood pressure during a hemodialysis treatment, but it can be counteracted by infusion of physiological saline solution.

For this reason, blood treatment machines on which a traditional infusion rod with a securing device designed as a so-called bottle stand mounted on it are widely used. Such an arrangement has the advantage that in addition to the blood treatment machine, it is not necessary to provide a separate infusion stand. The infusion rod attached to the blood treatment machine can be shifted in this way simultaneously with the blood treatment machine, which is usually mounted on stand elements designed as rollers, to adjust it to a variable position of the patient.

Since blood treatment machines may be of a considerable extent, this traditional arrangement has proven to be a disadvantage inasmuch as in this case the bottle stand is directly above the blood treatment machine. Access to the bottle stand may prove difficult here when mounting and removing items because the shortest access from beneath is not always directly accessible.

SUMMARY OF THE INVENTION

Therefore, the object of the present invention is to make available a blood treatment machine which permits simplified access to the securing means designed as a bottle stand, for example.

This object is achieved with a blood treatment machine that has a rod-shaped means attached thereto, with a securing means for securing objects that is connected to the rod-shaped means. Other advantageous embodiments of the present invention are described herein.

The inventive blood treatment machine has a housing and a blood treatment module, whereby vertical and horizontal directions are defined by the orientation of the housing during the use of the blood treatment machine. Furthermore, a rod-like means is attached to the blood treatment machine, its axial extent having at least one component running vertically to the housing. A securing means for securing articles is connected to the rod-shaped means. According to this invention the rod-shaped means has at least one first section and a second section, whereby the axial extent in the second section runs in a different direction than in the first section. This arrangement makes is possible to arrange the securing means in an area of the rod-shaped means that allows easier access from underneath. An embodiment in which the vertical projection of the center of gravity of the securing means runs next to the vertical projection of the housing is especially advantageous.

BRIEF DESCRIPTION OF THE DRAWINGS

Details of the invention are explained in greater detail on the basis of an exemplary embodiment shown in the drawings.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1:
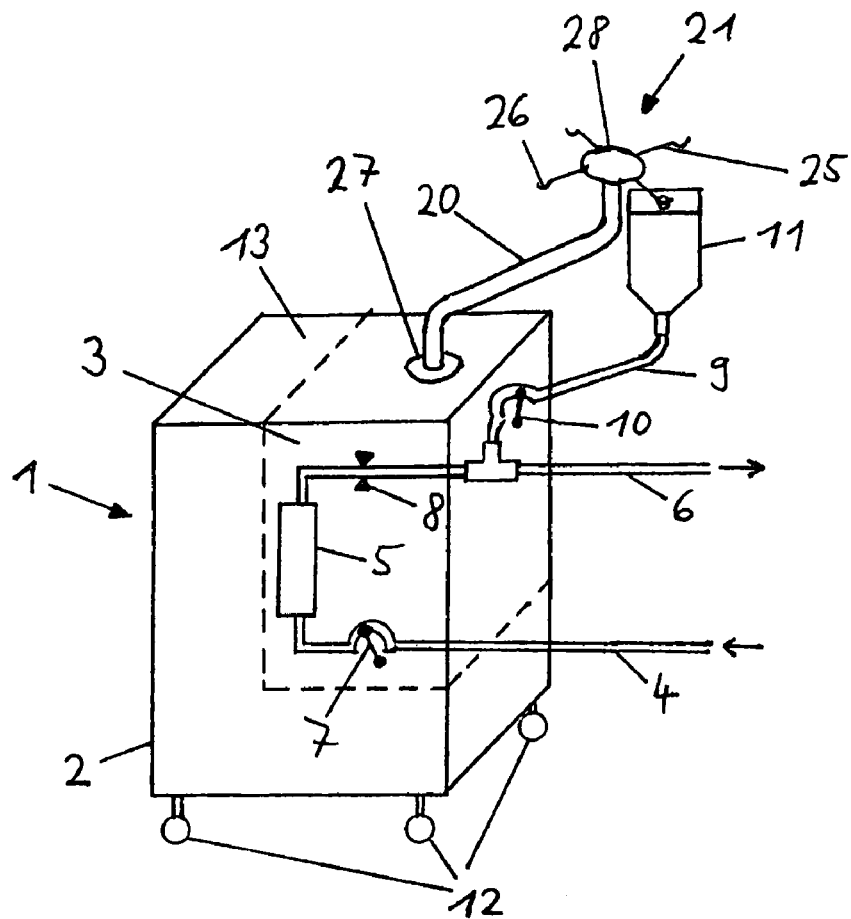
FIG. 1 shows a schematic diagram of an embodiment of an inventive blood treatment machine and FIG. 2 shows the individual sections of the rod-shaped means of the embodiment shown in FIG. 1.

FIG. 1 shows a blood treatment machine 1 having a housing 2 and a blood treatment module 3. The blood treatment module 3, the shape of which is indicated schematically by the dotted line, is suitable for holding components of an extracorporeal circulation. Of these, FIG. 1 shows a blood inlet line 4 leading from a patient (not shown) to a blood treatment element 5 and a blood return line 6 returning from the blood treatment element 5 to the patient. The blood treatment element may consist of a hemodialyzer or hemofilter divided by a semipermeable membrane into two chambers, for example. Such blood treatment elements are often designed in the form of hollow fiber modules which contain thousands of membrane fibers, the interior of which has extracorporeal blood flowing through it. For the sake of simplicity, FIG. 1 does not show the components of an extracorporeal blood circulation that pertain to the connection of lines for additional liquids such as dialysis fluid to the blood treatment element as well as other elements with which those skilled in the art are familiar.

The elements of the extracorporeal blood circulation, usually designed as disposable items, are connected to actuators and sensors of the blood treatment module 3, so that the blood treatment machine can control and monitor the actual blood treatment. Of these actuators and sensors, a blood pump 7 and a venous clamp 8 are shown here as examples. Blood is circulated in the extracorporeal circulation with the help of the blood pump 7. The venous clamp 8 serves to interrupt the flow in the extracorporeal circulation in the event of an alarm situation.

The housing 2 has stand elements 12 designed as rollers on the lower end so that the blood treatment machine can be shifted as needed. A rod-shaped means 20 is attached to the upper bordering surface 13 of the housing 2 by a rotary coupling 27. The rod-shaped means 20 extends axially with a component running vertically to the housing 2 starting from a first lower end, whereby the housing 2 defines the vertical and horizontal directions by being set up for use of the blood treatment machine. At the second upper end of the rod-shaped means 20 there are securing means 21, consisting of rods 25 arranged in the form of a cross in the embodiment illustrated in FIG. 1, these rods defining a plane horizontal to the housing 2. Hooks 26 for securing objects are provided at the ends of the rods 25. The rods 25 are attached to a securing block 28 that is in turn attached to the rod-shaped means 20.

As an example, an object 11 designed as a bag filled with infusion fluid is shown as being suspended from one of the hooks 27. The bag 11 is connected to a blood return line 6 via a connecting line 9 and a T connector piece. In this embodiment the connecting line 9 also leads via an infusion pump 10 provided on the blood treatment module 3 so that, if required, an infusion can be controlled by the blood treatment machine 1.

Figure 2:
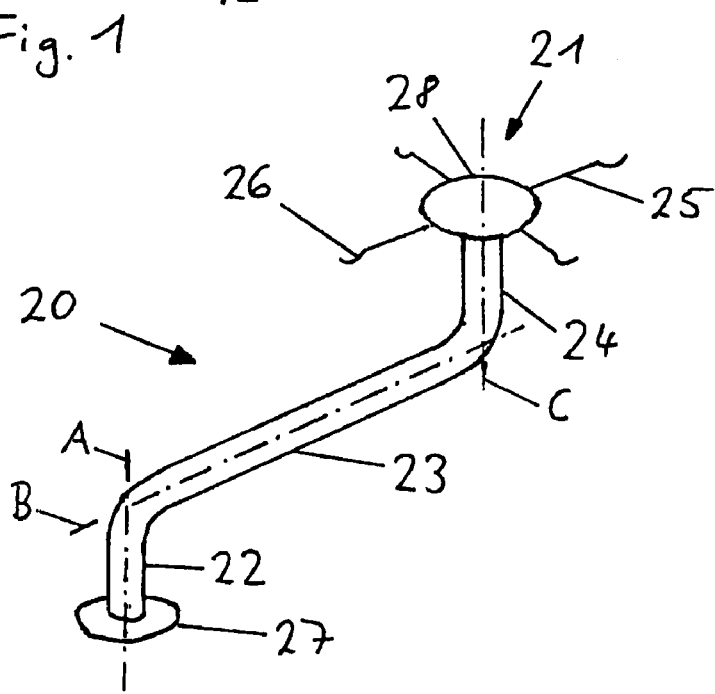

FIG. 2 shows the rod-shaped means 20 in detail. It consists of three sections 22, 23 and 24. The first section 22 is attached to the rotary coupling 27 at an axial extent A running vertically to the housing. A second section 23 is connected to this first section 22, its axial extent B extending in another direction than that of the first section. In this embodiment the axial extent B has a horizontal as well as a vertical component. This achieves the result that the perpendicular projection of the securing means 21 attached to the rod-shaped means 20 is shifted horizontally in relation to the fastening of the first section 22 to the housing 2. In the embodiment shown in FIG. 1, the vertical projection actually runs next to the vertical projection of the housing 2. The securing means 21 can therefore be more easily accessible from underneath.

In the embodiment shown in the drawings, a third section 24 is also connected to the second section 23 of the rod-shaped means 20, its axial extent C running parallel to the axial extent of the first section, i.e., in this embodiment the shape of the rod-shaped means 20 is cropped.

The rotary coupling 27 allows the entire rod-shaped means 20 to be swiveled over the upper bordering surface 13 of the blood treatment machine 1, should this be necessary, e.g., in conveyance of the blood treatment machine 1 or if it is appropriate in the individual case for reasons of space, for example, during a blood treatment.

The rod-shaped means 20 and/or the individual sections thereof may be designed in one piece or comprised of multiple components. It may then be possible for different vertical and horizontal course of the rod-shaped means 20 to be implemented by different components as needed, as is possible with a modular system.

The design of the inventive blood treatment machine thus allows simplified access to the securing means for bags containing medicinal solutions, for example, without having to sacrifice the advantages of a conventional device in which a vertical infusion rod is attached to the housing of the blood treatment machine.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. A blood treatment machine comprising a housing and a blood treatment module, whereby vertical and horizontal directions are defined by an orientation of the housing during use of the blood treatment machine, having a rod-shaped means attached to the blood treatment machine, an axial extent thereof having at least one vertical component in relation to the housing, and having a securing means connected to the rod-shaped means for securing containers with medical solutions, the rod-shaped means (i) having a cropped shape, with a first section, a second section, and a third section, whereby the axial extent in the second section runs in a different direction than in the first section, and the axial extent in the third section runs parallel to the first section, and (ii) being mounted on the blood treatment machine at an upper bordering surface of the housing by a rotary coupling to rotate about an axis of the first section and over the upper bordering surface of the housing.

2. The blood treatment machine according to claim 1, wherein the second section runs between the first section and a third section whereby the axial extent of the third section runs in a different direction than that of the second section.

3. The blood treatment machine according to claim 2, wherein the axial extent of the first section and the third section run in parallel directions.

4. The blood treatment machine according to claim 3, wherein the axial extent of the first section and the third section run in a vertical direction in relation to the housing.

5. The blood treatment machine according to claim 2, wherein the rod-shaped means has a first lower end and a second upper end, and wherein the securing means is connected to the second upper end of the rod-shaped means.

6. The blood treatment machine according to claim 1, wherein a vertical projection of a center of gravity of the securing means runs next to a vertical projection of the housing.

7. The blood treatment machine according to claim 1, wherein the securing means includes at least one of hook-shaped and rod-shaped fastening means.

8. The blood treatment machine according to claim 7, wherein the rod-shaped fastening means include rods arranged in a cross, defining a horizontal plane in relation to the housing.

9. The blood treatment machine according to claim 8, further comprising hooks provided on the ends of the rods for securing the medical solution containers.

10. The blood treatment machine according to claim 1, wherein the blood treatment module is configured to hold components of an extracorporeal blood circulation, including a blood supply line leading from a patient to a blood treatment element, and a blood return line leading back from the blood treatment element to the patient.

11. The blood treatment machine according to claim 10, wherein the blood treatment element is a hemofilter or a hemodialyzer that is divided by a semipermeable membrane into two chambers, with one of the chambers being connected to the blood supply line and the blood return line.

12. The blood treatment machine according to claim 10, further comprising at least one of actuators and sensors associated with the extracorporeal blood circulation.

13. The blood treatment machine according to claim 10, wherein the blood treatment module is configured to hold a line that carries a liquid and connects the secured medical solution container to the extracorporeal circulation.

14. The blood treatment machine according to claim 13, wherein the blood treatment module has at least one of actuators and sensors associated with the connected liquid carrying line.

15. The blood treatment machine according to claim 1, wherein the medical solution containers are bags that contain at least one of an infusion solution and a dialysis solution.

16. A blood treatment machine comprising:
a housing and a blood treatment module, with vertical and horizontal directions associated therewith being defined by an orientation of the housing during use of the blood treatment machine;
a single piece rod-shaped device attached to the blood treatment machine, an axial portion thereof having at least one vertical component in relation to the housing, the rod-shaped device having a cropped shape including a first section, a second section, and a third section, with the axial portion in the second section extending in a different direction than in the first section, and the axial portion in the third section extending in a direction parallel to that of the first section, the rod-shaped device being attached to an upper surface of the housing by a rotary coupling so as to rotate about an axis of the first section and over the upper surface of the housing; and
a securing device connected to the rod-shaped device to secure containers for medical solutions.

17. The blood treatment machine according to claim 16, wherein the third section extends upward from the second section and parallel to the first section.

18. The blood treatment machine according to claim 16, wherein the securing device includes at least one of hook-shaped and rod-shaped fasteners.

19. The blood treatment machine according to claim 18, wherein a vertical projection of a center of gravity of the securing device extends next to a vertical projection of the housing.

20. The blood treatment machine according to claim 17, wherein the rod-shaped device has a first lower end and a second upper end, and wherein the securing device is connected to the second upper end of the rod-shaped device.

* * * * *